United States Patent
Karube et al.

[11] Patent Number: 5,804,047
[45] Date of Patent: Sep. 8, 1998

[54] ENZYME-IMMOBILIZED ELECTRODE, COMPOSITION FOR PREPARATION OF THE SAME AND ELECTRICALLY CONDUCTIVE ENZYME

[75] Inventors: Isao Karube, 1-3-16, Higashi-Arima, Miyamae-Ku, Kawasaki-shi, Kanagawa-ken, Japan; Susan Anne Clark, Leatherhead, United Kingdom; Ryohei Nagata, Tokyo-to, Japan

[73] Assignees: Dai Nippon Printing Co., Ltd., Tokyo-to; Isao Karube, Kawasaki, both of Japan

[21] Appl. No.: 357,987

[22] Filed: Dec. 16, 1994

Related U.S. Application Data

[63] Continuation of Ser. No. 37,102, Mar. 26, 1993, abandoned.

[30] Foreign Application Priority Data

Mar. 31, 1992 [JP] Japan .................................. 4-108706
Sep. 10, 1992 [JP] Japan .................................. 4-269552

[51] Int. Cl.⁶ .................................................. G01N 27/26
[52] U.S. Cl. .............................. 204/403; 435/4; 435/11; 435/14; 435/26; 435/188; 435/190; 435/287.1; 435/289.1; 435/817
[58] Field of Search ............................. 204/403, 416, 204/418, 419, 415; 435/287.1, 289.1, 817, 4, 14, 26, 11, 188, 190; 252/502

[56] References Cited

U.S. PATENT DOCUMENTS 5,089,112  2/1992  Skotheim et al. ........................ 204/403

FOREIGN PATENT DOCUMENTS

| 0 126 043 | 11/1984 | European Pat. Off. . |
| 0 278 647 | 8/1988 | European Pat. Off. . |
| 0 294 294 | 12/1988 | European Pat. Off. . |
| 277 759 | 4/1990 | Germany . |
| 1-117781 | 5/1989 | Japan . |
| 85/05638 | 12/1985 | WIPO . |

OTHER PUBLICATIONS

European Search Report dated Jul. 14, 1993.

Mansson, Mats–Olle et al., "Covalent Binding of an NAD Analogue to Liver Alcohol Dehydrogenase Resulting in an Enzyme–Coenzyme Complex not Requiring Exogenous Coenzyme for Activity," Eur. J. Biochem., May 1978, 455–63.

*Primary Examiner*—Bruce F. Bell
*Attorney, Agent, or Firm*—Fish & Richardson, P.C.

[57] ABSTRACT

An enzyme sensor system capable of quantitatively determining a particular component contained in a biological sample in a rapid and easy manner is disclosed. More particularly, an electrically conductive enzyme, an enzyme-immobilized electrode using the same and a composition for use in the preparation of the enzyme electrode are disclosed. The composition for an enzyme-immobilized electrode according to the present invention enables electrodes of various patterns to be produced by screen printing.

7 Claims, 14 Drawing Sheets

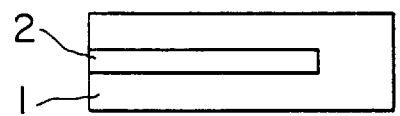
F I G. 2 (a)
F I G. 2 (b)
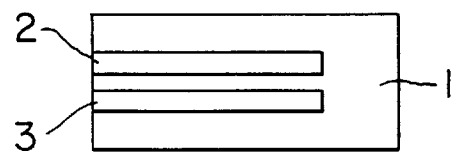
F I G. 2 (c)
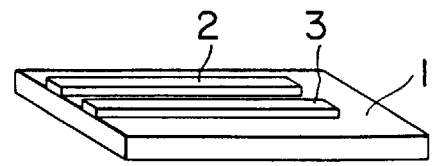
F I G. 2 (d)

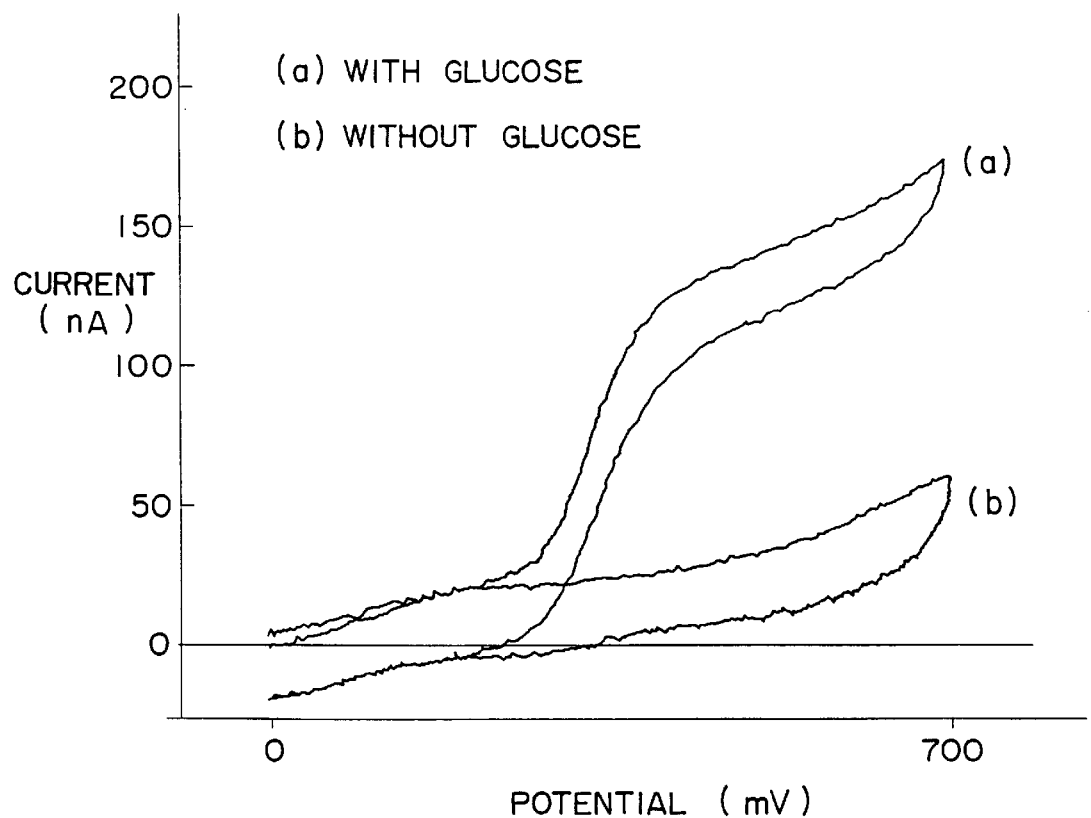
F I G. 6

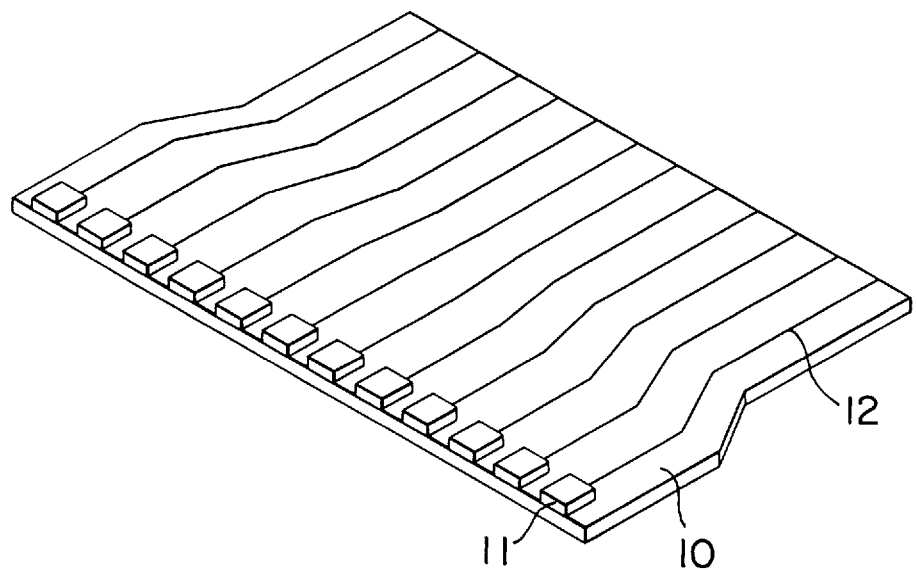
F I G. 13 (a)
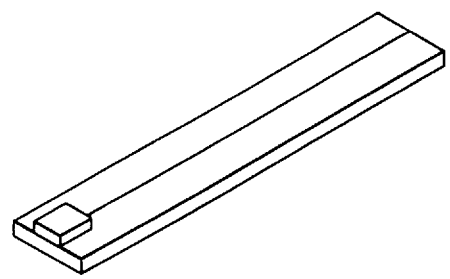
F I G. 13 (b)

ENZYME-IMMOBILIZED ELECTRODE, COMPOSITION FOR PREPARATION OF THE SAME AND ELECTRICALLY CONDUCTIVE ENZYME

This application is a continuation of U.S. application Ser. No. 08/037,102 filed Mar. 26, 1993, now abandoned.

BACKGROUND OF THE INVENTION

The present invention relates to an enzyme sensor capable of quantitatively determining a particular component contained in a biological sample in a rapid and easy manner. More particularly, it is concerned with an electrically conductive enzyme, an enzyme-immobilized electrode using the same and a composition which is used for the preparation of the enzyme electrode.

It is already known that enzyme sensors are a tool by which to measure the amount of various substances through a high specificity of enzymes for substrate. For example, a glucose sensor has been widely utilized because its quantitative analysis is one of the advantages in practical use.

In enzyme sensors, especially in practical use, when it is made of an oxidase, for example, an object substance is quantitatively determined by electrochemically detecting the formed hydrogen peroxide or hydrogen ion or the amount of consumed oxygen with a hydrogen peroxide electrode, a hydrogen ion electrode or an oxygen electrode.

In such as enzyme sensors, an enzyme having a high specificity for an object substance must be immobilized on a base material, the enzyme is brought into contact with an object substance contained in the sample, and the substance formed by the action of the enzyme is detected and quantitatively determined, for example, by an electrochemical method. For instance, the oxidase sensor comprises an enzyme membrane; comprised of an oxidase immobilized membrane, and a diaphragm oxygen electrode provided with the enzyme membrane on the surface thereof. When a target substance as the substrate is oxidized by the action of the immobilized enzyme, the electric current measured by the oxygen electrode shows the deviation according to the amount of the substrate which contacts with the enzyme membrane is varied. Thus, the concentration of the substrate can be determined by the electrochemical measurement technique.

Furthermore, it is another practice to allow a mediator to apply in a sensor system in such a manner that an enzyme reaction with the substrate that can be easily detected. For example, a proposal has been made on a method which comprises coating an artificial mediator on the surface of an electrode and covering the coating with a semitransparent film (EP-7863681). Further, a proposal has been made on a method wherein a mediator sparingly soluble in water is incorporated in an electrode (Agric. Biol. Chem., 52, 1557 (1988)) and a method which comprises previously incorporating a water-soluble mediator in an electrode and providing on the surface of the electrode a thin film comprising an ionic polymer and an enzyme to prevent the mediator from dissolving in the electrolyte (Agric. Biol. Chem., 52, 3187 (1988)). Further, a proposal has been made on a method wherein a paste prepared by mixing an enzyme and ferrocene in paraffin is pressed into an electrode (Talania, Vol. 38, No. 1, 107–110 (1991)).

However, the preparation for conventional electrodes used in enzyme sensors, especially enzyme-immobilized electrodes including a mediator, is generally troublesome. Therefore, in order to stably attain a good precision, close attention should be paid to the quality control of the electrode in the production process. Furthermore, it has been pointed out that the conventional sensors are unsatisfactory in the service life of the electrodes. In addition, the mediator leakage from the electrode causes serious trouble in the in vivo measurement. For this reason, when a mediator is allowed to adapt into the system, the stabilization of the mediator has been also one of the most important tasks to develop enzyme sensors.

SUMMARY OF THE INVENTION

Accordingly, an object of the present invention is to provide an enzyme-immobilized electrode for use as an enzyme sensor which can be easily prepared and exhibits a stable performance.

Another object of the present invention is to provide an electrically conductive enzyme for use in an enzyme-immobilized electrode and a composition for use in the production of the enzyme-immobilized electrode.

According to an aspect of the present invention, there is provided a composition for the preparation of an enzyme-immobilized electrode, comprising an electrically conductive enzyme, an electrically conductive component and a vehicle.

According to another aspect of the present invention, there is provided an enzyme-immobilized electrode comprising a base material and, supported thereon, the above-mentioned composition.

According to a further aspect of the present invention, there is provided an electrically conductive enzyme comprising an enzyme and a mediator attached to a side chain of an enzyme or an enzyme body through a covalent bond.

An electrode can be provided by supporting the composition according to the present invention on a base material by a printing technique such as screen printing. Therefore, the use of the composition according to the present invention enables an enzyme sensor electrode having a stable performance to be produced by a simple method. The composition according to the present invention is advantageous also in that electrodes of various patterns can be easily produced by screen printing. In an electrode provided by using the composition according to the present invention, since a mediator is immobilized on an enzyme, no leakage of mediator in a test sample occurs. Therefore, the electrode can advantageously exhibit a stable performance.

BRIEF DESCRIPTION OF THE DRAWINGS

FIG. 1 is a typical diagram showing a modified enzyme having a mediator attached to a modified enzyme having an enzyme, wherein

FIG. 2 is a diagram showing preferred embodiments of the present invention, wherein FIG. 2(a) is a diagram of a unipolar electrode produced by forming enzyme-immobilized electrode 2 on base material 1, FIG. 2(b) is a perspective view of the unipolar electrode shown in FIG. 2(a), FIG. 2(c) is a diagram showing a bipolar electrode produced by forming enzyme-immobilized electrode 2 on base material 1 and providing on the same base material 1 counter electrode 3 formed by applying the same composition as that for the electrode 2 except for the absence of an electrically conductive enzyme in the same manner as that used in the application of the composition for the electrode 2, and FIG. 2(d) is a perspective view of the bipolar electrode shown in FIG. 2(c);

FIG. 6 shows cyclic voltammograms of GOD prepared in Example 4 having ferrocene attached to its body and side chain;

FIG. 13 is a typical diagram of an electrode array and its one prepared in Example 17, wherein FIG. 13(a) shows a group of electrodes provided by forming twelve (12) electrodes on a base material by screen printing with number 10 designating a polyimide film, numeral 11 designating an electrode portion prepared from a composition for an enzyme-immobilized electrode and numeral 12 designating a copper foil and FIG. 13(b) is a diagram of an electrode cut off from the group of electrodes shown in FIG. 13(a);

PREFERRED EMBODIMENTS OF THE INVENTION

Composition for Enzyme Electrode

Figure 1A:
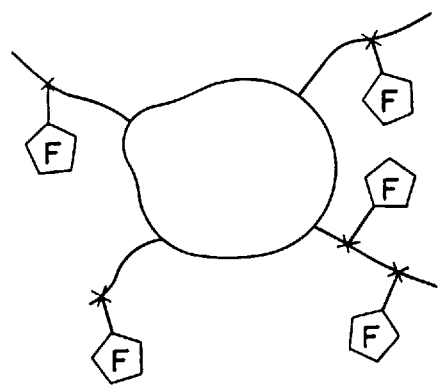
FIG. 1(a) shows a mediator attached to the side chain of the enzyme.

The composition for the preparation of an enzyme-immobilized electrode according to the present invention contains an enzyme which has a substrate specificity for an object substance and an electrical conductivity.

The term "electrically conductive enzyme" used herein is intended to mean an enzyme of which the electrical conductivity varies depending upon the amount of the object substance as a substrate present in the system. In the present invention, the electrically conductive enzyme include enzymes having an electrical conductivity in themselves and enzymes having an electrical conductivity imparted as a result of modification with various kinds of mediator.

The expression "enzymes having an electrical conductivity imparted as a result of modification with mediators" used herein is intended to mean the following enzymes. Since active sites of enzymes are generally present within proteins as enzymes, it is generally difficult to observe the donation and acceptance of electrons caused as a result of the action of enzymes from the outside, for example, through electrodes. In the case of oxidases, the donation and acceptance of electrons can be observed through the amount of consumed oxygen or the amount of the generated hydrogen ion or hydrogen peroxide. In many cases, however, it is difficult to stabilize these amounts in the system, so that these amounts are hard to serve as a measure which accurately reflects the amount of the substrate present in the system. However, the presence of a mediator serving as a medium of the movement of electrons between the active sites and the electrode (for example, by oxidation or reduction of the mediator per se) enables the electron movement caused in the active sites to be stably observed with a high accuracy by means of an electrode. Accordingly, the expression "an enzyme modified with a mediator" used in the present invention is intended to mean an enzyme to which an electrical conductivity has been imparted by the enzyme modified with a mediator which plays the function described above.

In the present invention, preferred examples of the electrically conductive enzyme include enzymes modified with the above-described mediator. The modified enzyme include three embodiments, that is, (1) an embodiment wherein a mediator is attached to a side chain (for example, an oligosaccharide chain, an alkyl chain, a peptide chain branched from a main chain, etc.) of the enzyme through a covalent bond, (2) an embodiment wherein a mediator is attached to the enzyme body through a covalent bond, and (3) an embodiment wherein a mediator is attached to the body and a side chain of the enzyme through a covalent bond. In these embodiments, the mediator and the enzyme may be bonded to each other through a suitable spacer.

In the present invention, the enzyme may be properly selected depending upon the relationship between the enzyme and an object substance to be determined. The mediator is not particularly limited so far as it plays the above-described role.

Preferred specific examples of the modified enzyme include oxidases or dehydrogenase modified with mediators. The oxidase is preferably selected from the group consisting of glucose oxidase, galactose oxidase, pyruvic acid oxidase, D- or L-amino acid oxidase, amine oxidase, cholesterol oxidase and choline oxidase. The dehydrogenase is preferably selected from the group consisting of alcohol dehydrogenase, glutamic acid dehydrogenase, cholesterol dehydrogenase, aldehyde dehydrogenase, glucose dehydrogenase, fructose dehydrogenase, sorbitol dehydrogenase and glycerol dehydrogenase. Preferred examples of the mediator include ferrocene, ferrocene derivatives, p-benzoquinoline, phenazine methosulfate, 2,6-dichlorophenolindophenol, pyrrolo-quinoline quinone (PPQ), flavin adenine dinucleotide (FAD), nicotinamide adenine nucleotide (NAD), and nicotinamide adenine dinucleotide phosphate (NADP) and so on. Ferrocene and its derivatives are particularly preferred. Preferred examples of the ferrocene derivative include 1,1'-dimethylferrocene, ferrocene acetic acid, hydroxymethylferrocene, 1,1'-bis (hydroxymethyl)ferrocene, ferrocenemonocarboxylic acid, ferrocene-1,1-dicarboxylic acid, chloroferrocene, methyltrimethylaminoferrocene.

Examples of the combination of the enzyme with the mediator include a combination of glucose oxidase with ferrocene or a ferrocene derivative.

More specifically, glucose-oxidase (GOD) catalyzes the following reaction

and the combination of glucose oxidase with ferrocene carries electrons as follows.

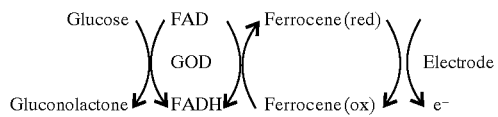

wherein FAD represents a flavin adenine dinucleotide.

The ferrocene as the mediator can be measured even at a lower electrode potential than one which has hydrogen peroxide, and is unaffected by many substances reducible at a potential similar to the potential at which hydrogen peroxide is reduced (for example, ascorbic acid).

In the introduction of the mediator into the oxidase or dehydrogenase, the mediator may be introduced into the enzyme body (for example, an amino group of a lysine residue) and/or side chain (for example, an oligosaccharide chain, an alkyl chain, a peptide chain branched from a main chain, etc.) of the enzyme of the oxidase or dehydrogenase.

It is also preferable to effect the introduction of the mediator through a suitable spacer. In particular, the introduction of the mediator into the side chain is preferably effected through a spacer. Preferred examples of the spacer include spacers represented by the following formula (I):

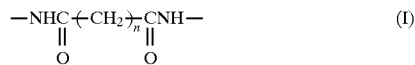

wherein n is an integer of 1 to 7.

Specific examples of the modified enzyme include one prepared by introducing a ferrocenecarboxylic acid into the enzyme body of an oxidase or dehydrogenase in its an amino group of a lysine residue through an acid amide bond and/or introducing a ferrocenecarboxylic acid through a spacer represented by the formula (I) by utilizing an aldehyde group formed by modifying an oligosaccharide chain of the enzyme.

The most preferred modified enzyme is an enzyme having ferrocene introduced into both the enzyme body and oligosaccharides in the above-described manner. This modified enzyme having a mediator introduced into the enzyme body and oligosaccharide is novel and exhibits particularly favorable properties in immobilized enzyme electrodes which will be described later. Therefore, the enzyme constitutes one embodiment of the present invention.

Although the amount of the mediator introduced into the enzyme is not particularly limited, it is preferably in the range of from about 1 to 50 based on one molecule of the enzyme. In particular, when the enzyme is oxidase or dehydrogenase and the mediator is ferrocene, the amount of the mediator is preferably in the range of from about 5 to 20, still preferably in the range of from about 10 to 15, based on one molecule of the enzyme.

Figure 1B:
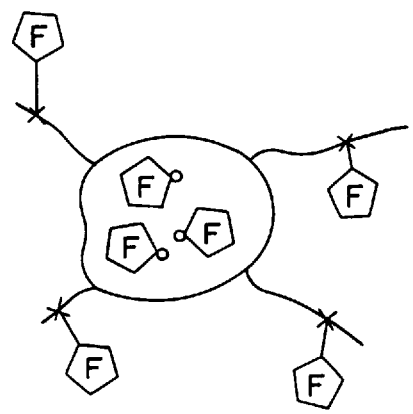
FIG. 1(b) shows a modified enzyme having a mediator attached to the body and side chain of the enzyme.
Figure 1C:
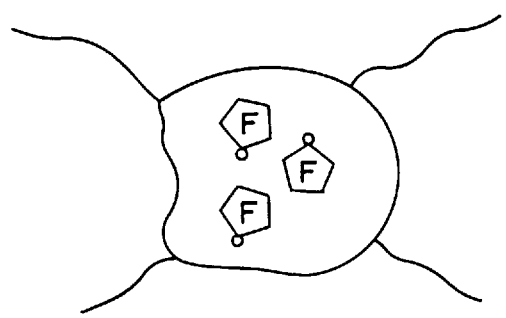
FIG. 1(c) shows a modified enzyme having a mediator attached to the body of the enzyme.

FIGS. 1(a), 1(b), and 1(c) are typical diagrams showing three kinds of modified enzyme having a mediator attached to the body and/or side chain of an enzyme.

The composition for the preparation of the enzyme-immobilized electrode according to the present invention contains an electrically conductive component besides the enzyme. Preferred examples of the electrically conductive component include a carbon powder, metal powder, such as gold and silver, polyion complex and electrically conductive polymer.

The composition according to the present invention is applied on a base material by the following method to fabricate an electrode. Therefore, proper components besides the enzyme and electrically conductive component are added in order to prepare the composition of the present invention. Specifically, an electrically conductive enzyme and an electrically conductive component are dispersed in a suitable vehicle to prepare a composition. Organic solvents are preferred as the vehicle. Specific examples of the vehicle include ethanol, propanol, butanol, isopropanol, pentanol, hexanol, butyl cellosolve, butyl cellosolve acetate, and benzene.

Furthermore, it is also preferable to add suitable additives to the composition of the present invention. Examples of such additives include pH buffers (for example, a citric acid/sodium citrate buffer), binder resins (for example, a polyvinyl butyral resin), surfactants (for example, a nonionic surfactant) and carriers (fillers) (for example, crystalline cellulose).

Other suitable additives to the composition of the present invention are disclosed in U.S. Pat. No. 5,183,742 and Japanese Laid-Open Publication Nos. 28199/91, 238763/85, 247967/86, 284661/86 and 263468/87, all of which are incorporated herein by reference. These Japanese publications relate to a composition for the preparation of diagnostic testing material. The compositions of the publications can contain some additives which are preferably used as additives (especially pH buffer, binder resin, surfactant, carrier and filler) to the composition according to the present invention.

The enzyme concentration in the composition according to the present invention is preferably 0.1 to 10%, still preferably 0.6%. The response characteristics of the sensor can be arbitrarily determined by varying the concentration of the enzyme. The concentration of the electrically conductive component is preferably 5 to 50%, particularly preferably 30%.

The composition of the present invention can be produced by mixing the above-described components by suitable means, for example, an agitator, a homomixer or a three-roll mill.

Production of Enzyme-Immobilized Electrode and Use Thereof

The composition according to the present invention is applied on a base material to provide an enzyme-immobilized electrode. Specifically, the composition is applied to a base material, and the vehicle component is removed by the evaporation to support the composition on the substrate. Although there is no particular limitation on the method for applying the composition on the base material, it is possible to apply printing techniques. For example, the composition can be applied to the base material by techniques such as screen printing, roller coating and dispenser. Screen printing is particularly preferred because various patterns can be relatively easily printed.

The enzyme-immobilized electrode thus produced can be utilized as an electrode for a sensor used in the measurement of the amount of presence of the substrate. The electrical conductivity of the enzyme-immobilized electrode varies depending upon the amount of presence of the substrate in a specimen sample through the immobilized enzyme. Therefore, when the change in the electrical conductivity is standardized in a system having a known substrate concentration, the substrate concentration of a sample of which the substrate concentration is unknown can be determined based on the results. More specifically, for this purpose, the substrate concentration and the change in the electrical conductivity of the immobilized enzyme electrode may be measured in a system comprising the immobilized enzyme electrode according to the present invention, a counter electrode and a reference electrode.

Figure 3A:
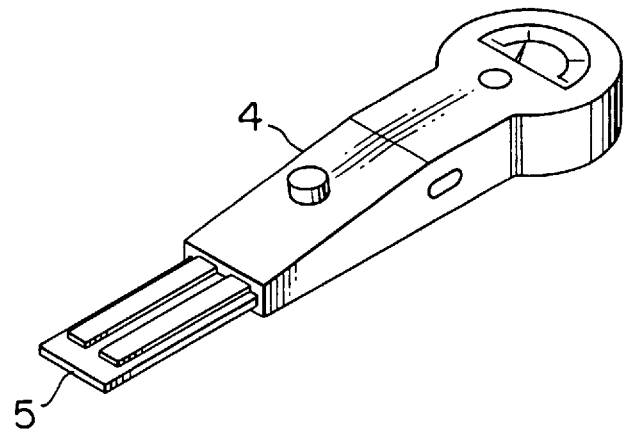
FIG. 3(a) is a typical diagram of a sensor equipped with a sensor electrode according to the present invention.
Figure 3B:
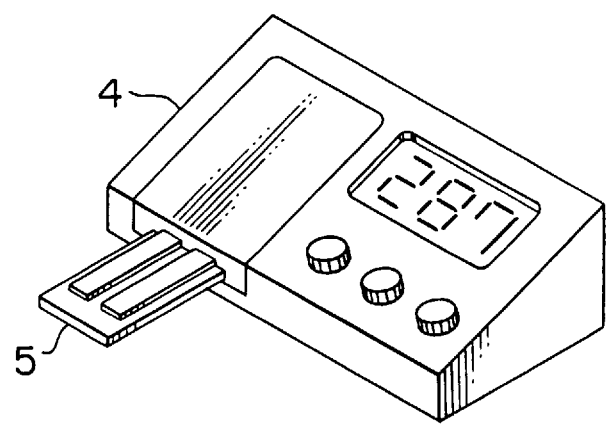
FIG. 3(b) is a typical diagram of a sensor equipped with a sensor electrode according to the present invention.
Figure 4:
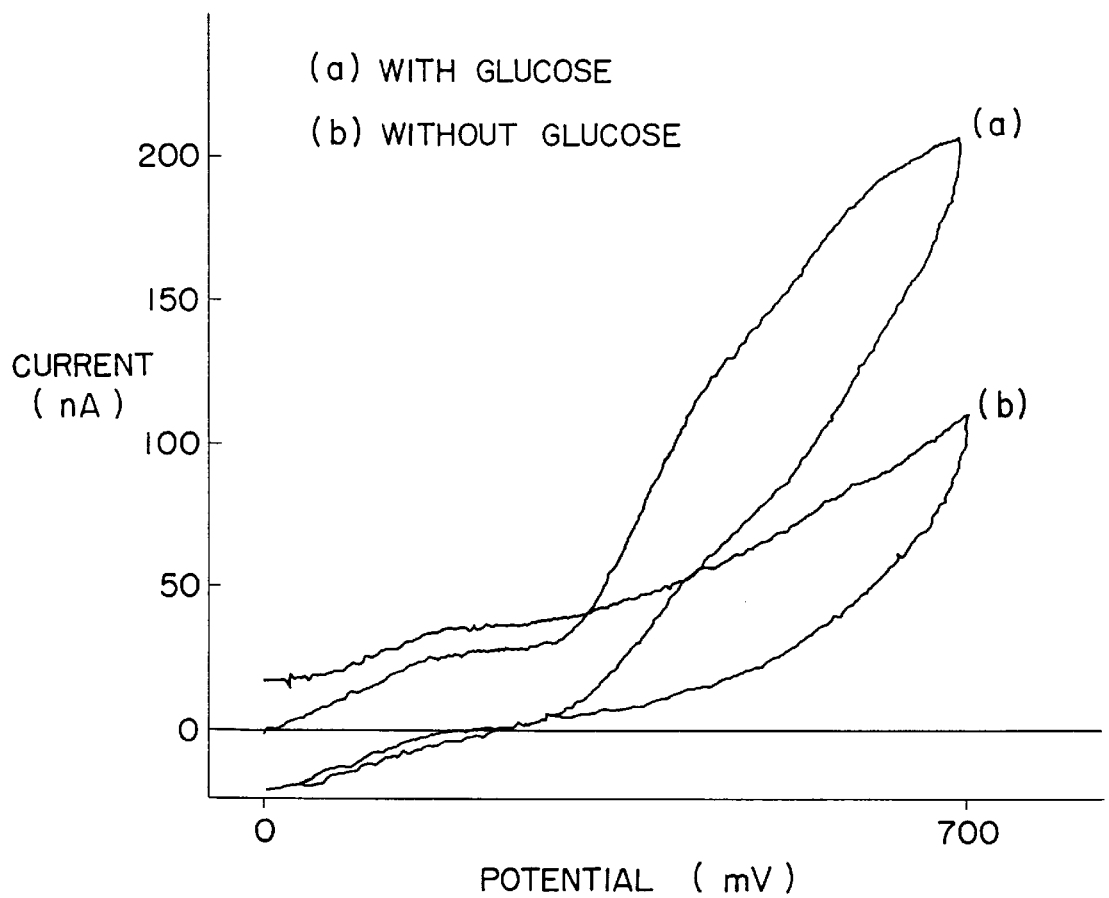
FIG. 4 shows cyclic voltammograms of GOD prepared in Example 1 having ferrocene attached to its side chain.

FIGS. 2(a), 2(b), 2(c) and 2(d) show preferred embodiments of an electrode for a sensor. FIG. 2(a) is a diagram of a unipolar electrode produced by applying a composition for an enzyme electrode to a base material 1 by screen printing to fabricate enzyme-immobilized electrode 2. FIG. 2(b) is a perspective view of the unipolar electrode shown in FIG. 2(a). FIG. 2(c) is a diagram showing a bipolar electrode produced by applying a composition for an enzyme electrode to base material 1 by screen printing to form enzyme-immobilized electrode 2 and providing on the same base material 1 counter electrode 3 formed by applying the same composition as that for the electrode 2 except for the absence of an electrically conductive enzyme in the same manner as that used in the application of the composition for the electrode 2. FIG. 2(d) is a perspective view of the bipolar electrode shown in FIG. 2(c). In the embodiments shown in FIGS. 2(c) and (d), the base material should consist an insulating material. FIGS. 3(a) and (b) are typical diagrams of sensors equipped with the above-described sensor electrodes. The electrode 5 is detachable from the body 4, and the electrode 5 may be of a disposable type.

Production of Electrically Conductive Enzyme

When the enzyme, as such, does not have an electrical conductivity, the electrical conductivity can be imparted by introducing a mediator into the enzyme. As described above, the mediator can be introduced into any of the body and side chain of the enzyme. Furthermore, the mediator can be introduced also by reacting a functional group present in the enzyme body or side chain (this functional group being one formed by oxidizing or reducing the enzyme or subjecting a functional group present in the enzyme to a substitution reaction with another functional group) with a functional group present in the mediator (this functional group being one formed by oxidizing or reducing the mediator or subjecting a functional group present in the mediator to a substitution reaction with another functional group).

Also in the case of the introduction through a spacer of the mediator, the introduction can be effected through the utilization of a functional group or the spacer.

Specific examples of the reaction where the enzyme is an oxidase or a dehydrogenase are as follows.

(1) Introduction of enzyme into side chain of enzyme:

At the outset, oligosaccharides of the oxidase or dehydrogenase is oxidized with a suitable oxidizing agent (for example, sodium periodate) in such a solvent as will not change the properties of the enzyme (for example, a phosphate buffer) to form an aldehyde group in the sugar chain. Subsequently, a dihydrazide represented by the following formula (II) is introduced as a spacer into the aldehyde:

$$H_2NNHC(CH_2)_nCNHNH_2 \quad \text{(II)}$$
$$\underset{O}{\|} \quad \underset{O}{\|}$$

The reaction product is reacted with ferrocenecarboxylic acid as a mediator in the presence of a suitable reducing agent (for example, sodium cyanoborohydride) or a condensing agent (for example, a carbodiimide).

(2) Introduction of mediator into body and side chain of enzyme (method A):

At the outset, a mediator is introduced into oligosaccharides of the enzyme in the same manner as that described in the above (1). Subsequently, the enzyme is treated with a modifier (for example, urea) to expose the inside of the protein, and ferrocenecarboxylic acid is introduced into the body and side chain of the enzyme by a method similar to a carbodiimide method described in Y. Degani and A. Heller (J. Physical Chemistry, 91, 1285–1289 (1987).

(3) Introduction of mediator into body and side chain of enzyme (method B):

At the outset, oligosaccharides of the enzyme is oxidized in the same manner as that described in the above (1) to form an aldehyde group in the side chain. Then, a dihydrazide represented by the formula (II) is introduced into the side chain of the enzyme in the presence of a modifier and a condensing agent. The enzyme subjected to modification and having a spacer on its side chain is reacted with ferrocenecarboxylic acid.

(4) Introduction of mediator into body of enzyme:

The introduction of mediator into body of enzyme can be effected according to the method described in the above (2). Specifically, the enzyme is treated with a modifier to expose the inside of the protein, and ferrocenecarboxylic acid is introduced into the body of the enzyme by a method similar to the carbodiimide method.

EXAMPLES

The present invention will now be described in more detail with reference to the following Examples, though it is not limited to these Examples only.

In the Examples, the following abbreviations are used; GOD: glucose oxidase, FDH: fructose dehydrogenase, and HEPES: N-2-hydroxyethylpiperazine-N'-2-ethanesulfonic acid.

EXAMPLE 1

(Introduction of Ferrocene into Side Chain of GOD (1))

(a) GOD (available from Sigma Chemical Co., Type II, EC1.1.3.4, *Aspergillus niger*, 100 mg) was dissolved in a 0.1M phosphate buffer (pH 6.0, 1 ml) and mixed with a solution of 20 mM sodium periodate previously dissolved in the same buffer as that described above, and the mixture was allowed to stand at 4° C. for one hr. Then, ethylene glycol (100 μl) was added thereto to terminate the oxidation reaction. Thereafter, the reaction mixture was further allowed to stand at 4° C. for 30 min, and then dialyzed over a period of 48 hr or more by using a 0.1M phosphate buffer (pH 6.0) as an external solution. In the dialysis, the external solution was replaced four times with a fresh external solution.

(b) Adipyl hydrazide (100 mg, a dried powder) was dissolved in the solution subjected to the dialysis, and the solution was allowed to stand at room temperature in a dark place overnight. The solution was then dialyzed by using a 0.1M phosphate buffer (pH 6.0) as an external solution. In the dialysis, the external solution was replaced four times with a fresh external solution to remove adipyl hydrazide remaining unreacted.

(c) Ferrocenecarboxyaldehyde (concentration: 1 mg/ml, pH: 6.0, 0.1M phosphate buffer: 2 ml) was mixed with the GOD hydrazide solution (2 ml) prepared in the above (b), and a reaction was allowed to proceed at 4° C. in a dark place overnight. Sodium cyanoborohydride was mixed therein to a final concentration of 10 mM, and a reaction was allowed to proceed for one hour. The reaction mixture was dialyzed by using a 0.1M phosphate buffer (pH 6.0) as an external solution. In the dialysis, the external solution was replaced four times with fresh external solution to remove excess ferrocenecarboxyaldehyde, thereby providing GOD having ferrocene introduced into its side chain.

EXAMPLE 2

(Introduction of Ferrocene into Side Chain of GOD (2))

(a) GOD (available from Sigma Chemical Co., Type II, EC1.1.3.4, *Aspergillus niger*, 500 mg) was dissolved in a 0.1M phosphate buffer (pH 6.0, 5 ml), and the solution was well stirred at 4° C. with caution so as not to give rise to foaming, and mixed with a solution of 20 mM sodium periodate previously dissolved in the same buffer as that described above. The mixture was allowed to stand at 4° C. for one hr. Then, ethylene glycol (500 μl) was added thereto, and the mixture was stirred at 4° C. for 30 min to terminate the reaction. Thereafter, the reaction mixture was dialyzed over a period of 48 hr or more by using a 0.1M phosphate buffer (pH 6.0) as an external solution. In the dialysis, the external solution was replaced four times with fresh external solution.

(b) Adipyl hydrazide (500 mg, a dried powder) was dissolved in the solution subjected to the dialysis, and the solution was allowed to stand at 4° C. in a dark place overnight. The solution was then dialyzed by using a 0.1 M phosphate buffer (pH 6.0) as an external solution over a period of 48 hr or more. In the dialysis, the external solution was replaced four times with fresh external solution to remove adipyl hydrazide remaining unreacted.

(c) 1-Ethyl-3-(dimethylaminopropyl)carbodiimide (500 mg) and ferrocenecarboxylic acid (450 mg) were previously dissolved in 0.15M HEPES buffer (25 ml) and regulated to a pH value of 7.3. This ferrocene solution was mixed with the enzyme solution subjected to the above-described dialysis, and the mixture was stirred at 4° C. in a dark place overnight while confirming several times that the pH value was 7.3. The stirred enzyme solution was again dialyzed by using a 0.1M phosphate buffer (pH 6.0) as an external solution over a period of 48 hr or more. In the dialysis, the external solution was replaced four times with fresh external solution to remove unreacted ferrocenecarboxylic acid and other low-molecular weight components to provide GOD having ferrocene introduced into its side chain.

EXAMPLE 3

(Introduction of Ferrocene into Body and Side chain of GOD (1))

(a) Ferrocene was introduced into the body and side chain of GOD with reference to a method described in Y. Degani and A. Heller (J. Physical and Chemistry, 91, 1285–1289 (1987)). Specifically, ferrocenecarboxylic acid and a free amino group of the enzyme per se were reacted with each other by a carbodiimide method to bond ferrocene to the body of GOD.

(a) The side chain of GOD was oxidized with sodium periodate in the same manner as that of Example 1(a).

(b) Adipyl hydrazide was reacted with the oxidized GOD in the same manner as that of Example 1(b).

(c) Urea (810 mg), a water-soluble carbodiimide (1-ethyl-3-(3-dimethylaminopropyl)carbodiimide hydrochloride; 100 mg) and ferrocenecarboxylic acid (80 mg) were subjected to sonication in a 0.15M HEPES buffer (4 ml, pH 7.3), and the mixture subjected to sonication was again adjusted to a pH value of 7.2 to 7.3. the ferrocenecarboxylic acid was saturated at this pH value. The GOD hydrazide solution (2 ml) prepared in the above (b) was added thereto, the pH value was confirmed and adjusted according to need, and the reaction mixture was allowed to stand at 0° C. in a dark place overnight. The reaction mixture was dialyzed by using a 0.1M phosphate buffer (pH 6.0) as an external solution. In the dialysis, the external solution was replaced four times with fresh external solution to remove excess reagents, thereby providing GOD having ferrocene introduced into its body and side chain.

An electrically conductive enzyme was prepared in the same manner as that described above, except that succinyl hydrazide (n=2) was used instead of adipyl hydrazide (n=4).

COMPARATIVE EXAMPLE 1

The preparation of an electrically conductive enzyme was attempted in the same manner as that of Example 3, except that oxalyl hydrazide (n=0) and sebacyl hydrazide (n=8) were used as a spacer instead of the adipyl hydrazide (n=4). Since, however, the spacer was not dissolved in the phosphate buffer for GOD, no electrically conductive enzyme could be prepared.

EXAMPLE 4

(Introduction of Ferrocene into Body and Side Chain of GOD (2))

Adipyl hydrazide was reacted with both an aldehyde group (—CHO) on the oxidized side chain of the enzyme and a free carboxyl group (—COOH) in the body of the enzyme, and the ferrocenealdehyde was reacted with hydrazide.

(a) Part of the side chain of GOD was oxidized with sodium periodate in the same manner as that of Example 1(a).

(b) 0.5M adipyl hydrazide (adjusted to pH 5: 2 ml), sodium chloride (9 mg), the oxidized GOD solution (2 ml) prepared in the above item (a), 1M water-soluble carbodiimide (1 ml) and 3M urea were mixed with each other, and the mixture was adjusted to a pH value of 5. Then, the mixture was allowed to stand at room temperature in a dark place for 4 hr to allow the reaction to proceed. The pH value was adjusted to 5 for every 30 min. 4 hr after the initiation of the reaction, the reaction mixture was dialyzed by using a 0.1M phosphate buffer (pH 6.0) as an external solution. In the dialysis, the external solution was replaced four times with fresh external solution.

(c) The GOD hydrazide solution (2.5 ml) prepared in the above (b) was mixed with 0.4 mg/ml ferrocenecarboxyaldehyde (2.5 ml), and the mixture was allowed to react at 4°

C. for 4 hr. Sodium cyanoborohydride was added thereto to a final concentration of 0.1 mM, and the mixture was dialyzed by using a 0.1M phosphate buffer (pH 6.0) as an external solution. In the dialysis, the external solution was replaced four times with a fresh external solution to provide GOD having ferrocene introduced into its body and side chain.

EXAMPLE 5

(Introduction of Ferrocene into Body and Side Chain of GOD (3))

(a) GOD (500 mg) was dissolved in a 0.1M phosphate buffer (pH 6.0, 5 ml), and the solution was well stirred at 4° C. with caution so as not to give rise to foaming and mixed with a solution of 20 mM sodium periodate previously dissolved in the same buffer as that described above. The mixture was allowed to stand at 4° C. for one hr. Then, ethylene glycol (500 µl) was added thereto, and the mixture was stirred at 4° C. for 30 min to terminate the reaction. Thereafter, the reaction mixture was dialyzed over a period of 48 hr or more by using a 0.1M phosphate buffer (pH 6.0) as an external solution. In the dialysis, the external solution was replaced four times with fresh external solution.

(b) Adipyl hydrazide (500 mg of a dried powder) was dissolved in the solution subjected to the dialysis, and the solution was allowed to stand at 4° C. in a dark place overnight. The solution was then dialyzed by using a 0.1 M phosphate buffer (pH 6.0) as an external solution over a period of 48 hr or more. In the dialysis, the external solution was replaced four times with fresh external solution to remove adipyl hydrazide remaining unreacted.

(c) Urea (4050 mg), 1-ethyl-3-(dimethylaminopropyl) carbodiimide (500 mg) and ferrocenecarboxylic acid (450 mg) were dissolved in 0.15M HEPES buffer (25 ml) and regulated to the pH value of 7.3. This ferrocene solution was mixed with the enzyme solution subjected to the above-described dialysis, and the mixture was stirred at 4° C. in a dark place overnight while confirming several times that the pH value was 7.3. The stirred enzyme solution was again dialyzed by using a 0.1M phosphate buffer (pH 6.0) as an external solution over a period of 48 hr or more. In the dialysis, the external solution was replaced four times with fresh external solution to remove unreacted ferrocenecarboxylic acid and other low-molecular weight components to provide GOD having ferrocene introduced into its side chain.

EXAMPLE 6

(Introduction of Ferrocene into Body of GOD (1))

GOD (100 mg) was dissolved in a 0.1M phosphate buffer (1 ml, pH 6.0), and the mixture was well stirred at 4° C.

Urea (810 mg), a water-soluble carbodiimide (1-ethyl-3-(3-dimethylaminopropyl)carbodiimide hydrochloride; 100 mg) and ferrocenecarboxylic acid (80 mg) were subjected to sonication in a 0.15M HEPES buffer (4 ml, pH 7.3), and the mixture subjected to sonication was again adjusted to the pH value of 7.2 to 7.3. The ferrocenecarboxylic acid was saturated at this pH value. The GOD solution was added thereto, the pH value was confirmed and adjusted according to need, and the reaction mixture was allowed to stand at 0° C. in a dark place overnight. The reaction mixture was dialyzed by using a 0.1M phosphate buffer (pH 6.0) as external solution. In the dialysis, the external solution was replaced four times with a fresh external solution to remove excess reagents, thereby providing GOD having ferrocene introduced into its body.

EXAMPLE 7

(Introduction of Ferrocene into Body of GOD (2))

GOD (500 mg) was dissolved in a 0.1M phosphate buffer (5 ml, pH 6.0), and the mixture was well stirred at 4° C.

Urea (4050 mg), (1-ethyl-3-(3-dimethylaminopropyl) carbodiimide hydrochloride (500 mg) and ferrocenecarboxylic acid (450 mg) were dissolved in a 0.15M HEPES buffer (25 ml). The solution was adjusted to the pH value of 7.3. The GOD solution was added thereto, and the mixture was allowed to stand at 4° C. in a dark place overnight while confirming several times that the pH value was 7.3. The reaction mixture was dialyzed by using a 0.1M phosphate buffer (pH 6.0) as external solution. In the dialysis, the external solution was replaced four times with fresh external solution to remove excess reagents, thereby providing GOD having ferrocene introduced into its body.

EXAMPLE 8

(Introduction of Ferrocene into Side Chain of FDH)

The introduction of ferrocene was effected in the same manner as that of Example 2, except that FDH was used instead of GOD.

EXAMPLE 9

(Introduction of Ferrocene into Body and Side Chain of FDH)

The introduction of ferrocene was effected in the same manner as that of Examples 3 and 4, except that FDH was used instead of GOD.

EXAMPLE 10

(Introduction of Ferrocene into Body of FDH)

The introduction of ferrocene was effected in the same manner as that of Example 6, except that FDH was used instead of GOD.

EXAMPLE 11

(Evaluation of Electrically Conductive Enzyme (1))

Electrically conductive enzymes prepared in the above Examples were evaluated with a cyclic voltammetry using a gold working electrode (diameter: 1 mm), a platinum counter electrode and a Ag/AgCl reference electrode. The working electrode was polished by aluminum oxide (0.075 µm) prior to use. The measurement was conducted with Hokuto Denshi potentiostat/Galvanostat (Model HAB-151) and Graphtec WX1200 recorder.

The modified enzyme solutions prepared in the Examples, as such, were used without dilution. In order to prevent interference with hydrogen peroxide, catalase was added thereto to a final concentration of 0.1 mg/ml. At the outset, the cyclic voltammogram of the electrically conductive enzyme was measured in the absence of a substrate. Then, a glucose or fructose solution was added to a final concentration of 10 mM, and the cyclic voltammogram was measured under the same conditions. Bubbling with nitrogen was sufficiently effected during the measurement for the purpose of eliminating the influence of oxygen.

The results of measurement for the electrically conductive enzymes prepared in Examples 1, 2, 3 (spacer: adipyl hydrazide), 5, 6 and 7 are shown in FIGS. 4, 5, 6, 7, 8 and 9, respectively. As is apparent from these drawings, the addition of glucose as a substrate caused the electrical conductivity to be increased.

In the case of Examples 2, 5 and 7, the gold electrode had a diameter of 5 mm, and a glucose solution was added to a final concentration of $8.25 \times 10^{-2}$ mM.

EXAMPLE 12

(Evaluation of Electrically Conductive Enzyme (2))

Two electrically conductive enzymes (spacer: adipyl hydrazide (n=4) and succinyl hydrazide (n=2)) prepared in Example 3 were evaluated. The cyclic voltammogram was measured in the same manner as that of Example 11, except that the glucose solution was added to a final concentration of 1.0 mg/ml.

Figure 10:
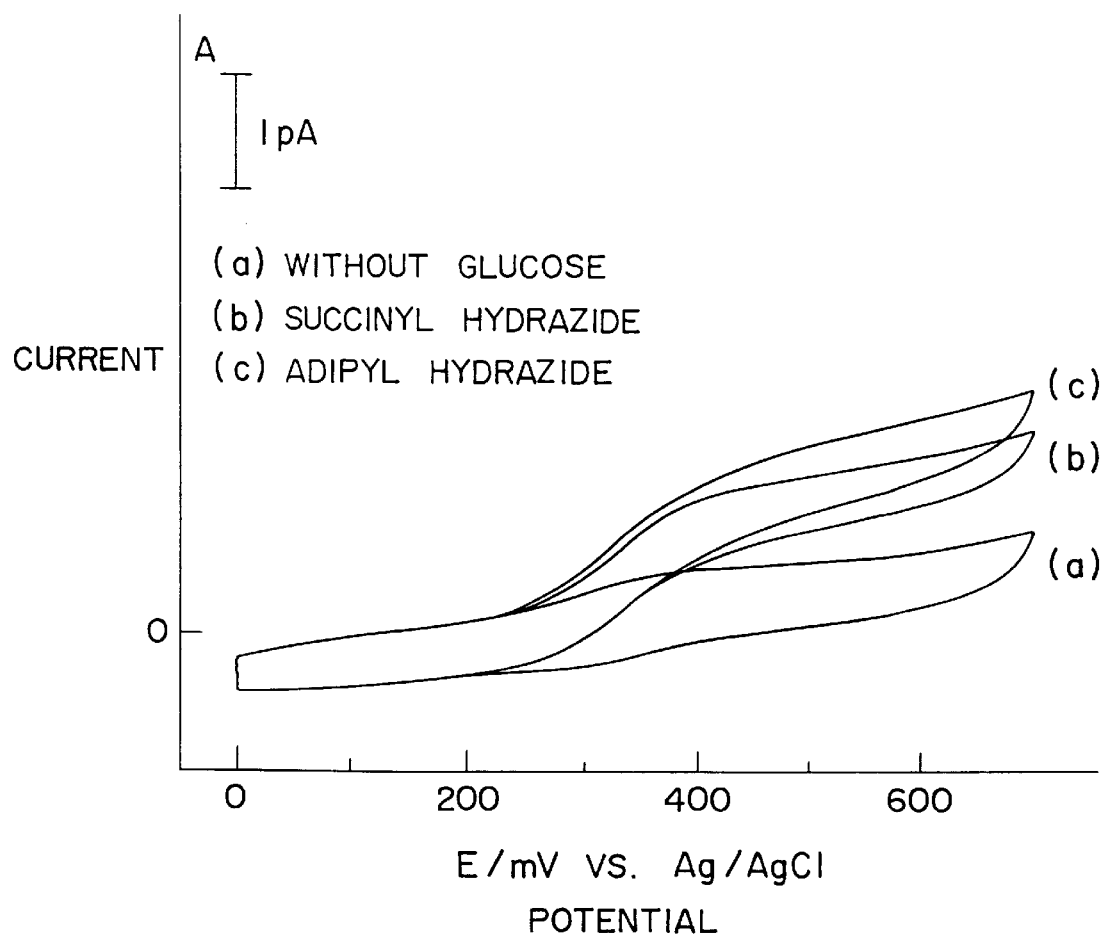
FIG. 10 shows cyclic voltammograms of GOD prepared in Example 3 having ferrocene attached to its body and side chain, wherein the number of carbon atoms, n, of the spacer is 2 or 4.

The results are given in FIG. 10. As is apparent from the drawing, the electrically conductive enzyme, wherein adipyl hydrazide was used as the spacer, exhibited a higher response than the electrically conductive enzyme wherein succinyl hydrazide was used as the spacer.

EXAMPLE 13

(Evaluation of Electrically Conductive Enzyme (3))

The electrically conductive enzyme (spacer: adipyl hydrazide) prepared in Example 3 was evaluated by measuring a cyclic voltammogram in final glucose concentrations of 0, 0.02, 0.06 and 0.08 mg/ml. The measurement was effected in the same manner as that of Example 11, except that the concentration of glucose was varied.

Figure 11:
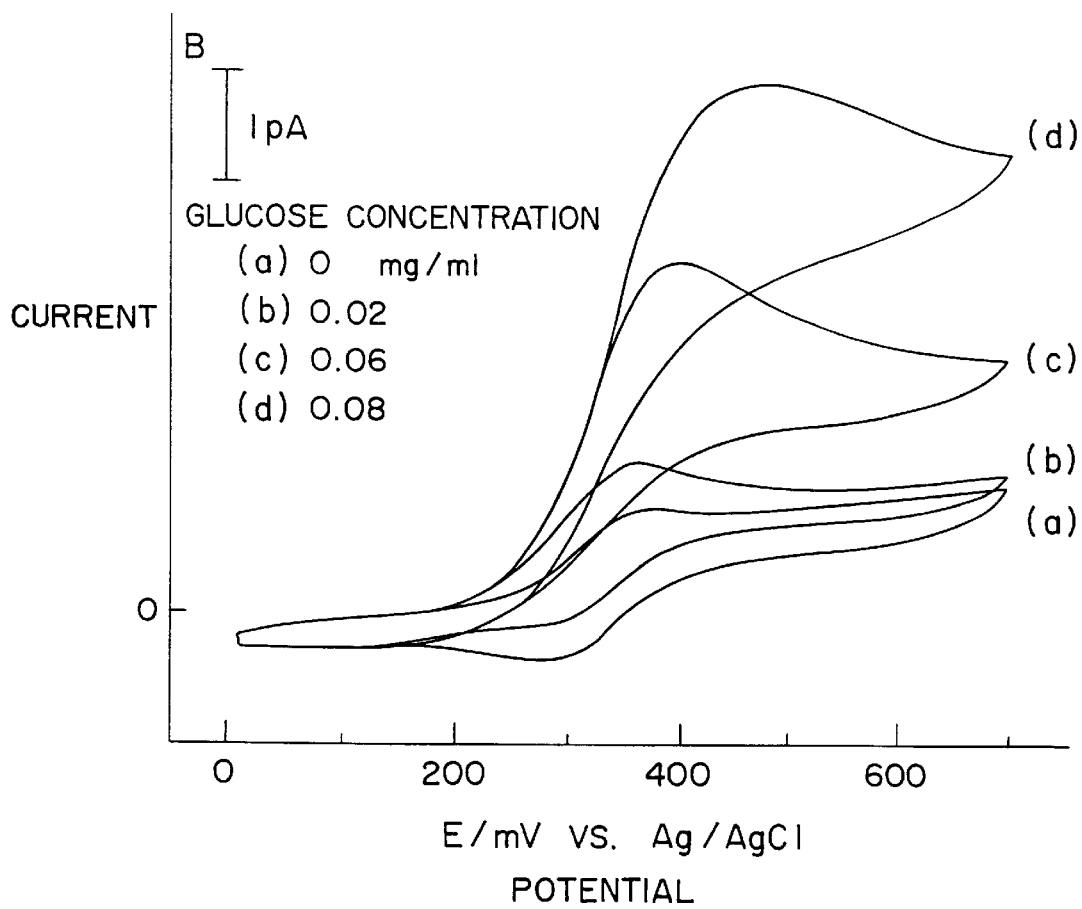
FIG. 11 shows cyclic voltammograms of GOD prepared in Example 3 having ferrocene attached to its body and side chain with the concentration of glucose being varied.

The results are given in FIG. 11. As is apparent from the drawing, a positive correlation was observed between the glucose concentration and the increase in the electrical conductivity in a solution system containing an electrically conductive enzyme.

EXAMPLE 14

(Evaluation of Electrically Conductive Enzyme (4))

Figure 5:
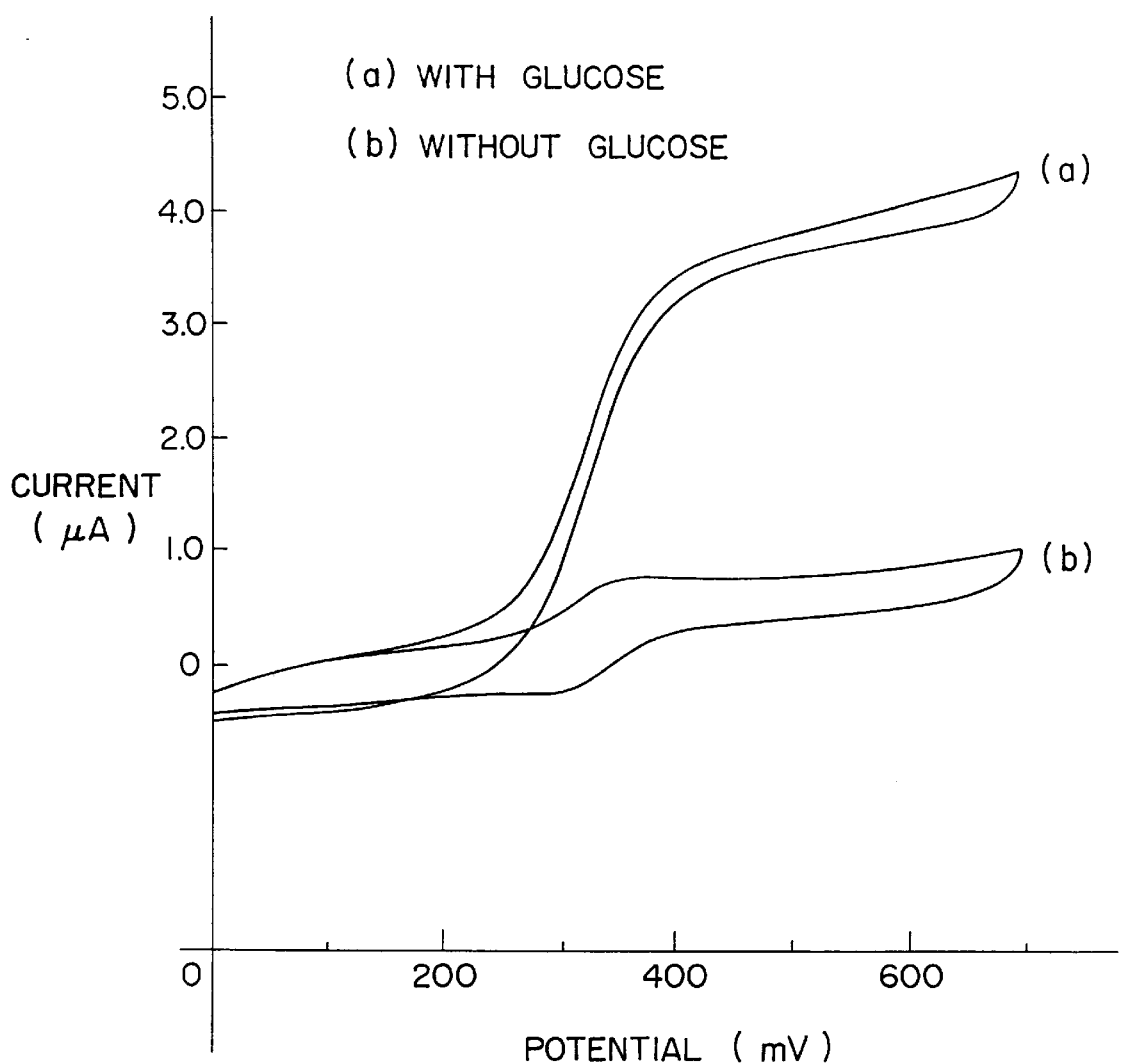
FIG. 5 shows cyclic voltammograms of GOD prepared in Example 2 having ferrocene attached to its side chain.
Figure 7:
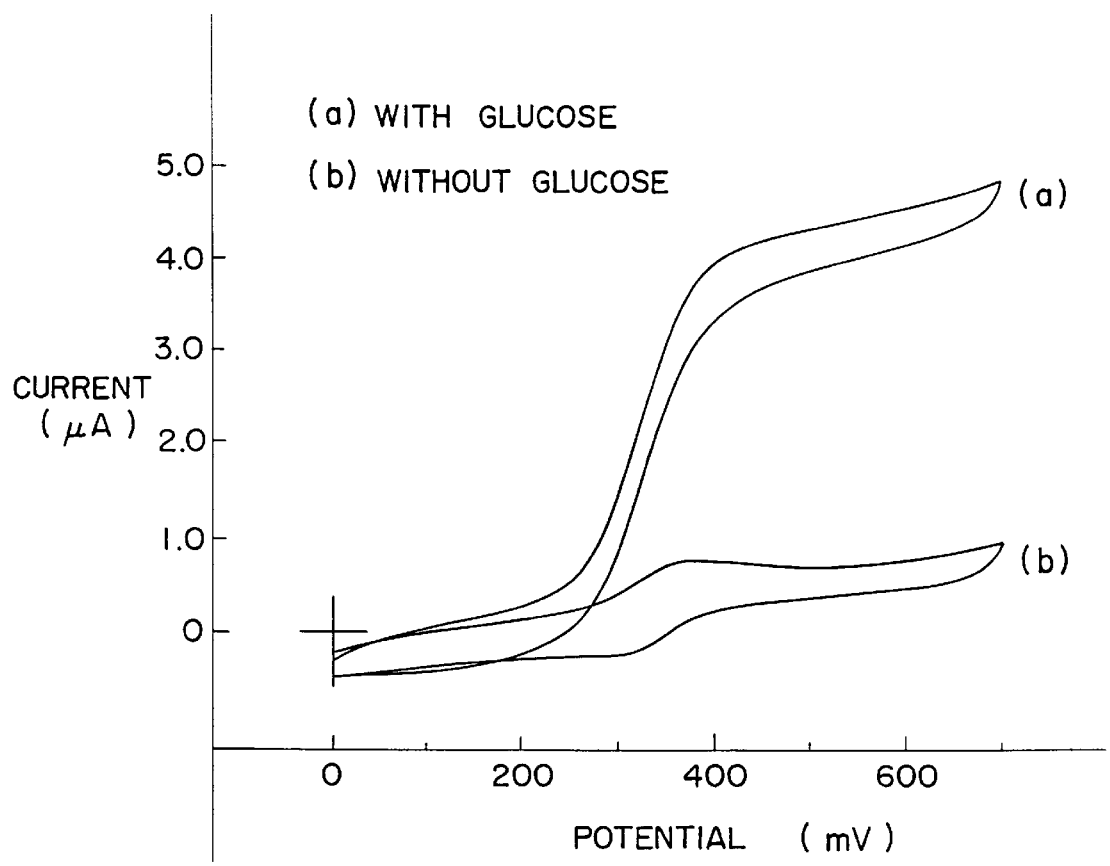
FIG. 7 shows cyclic voltammograms of GOD prepared in Example 5 having ferrocene attached to its body and side chain.
Figure 8:
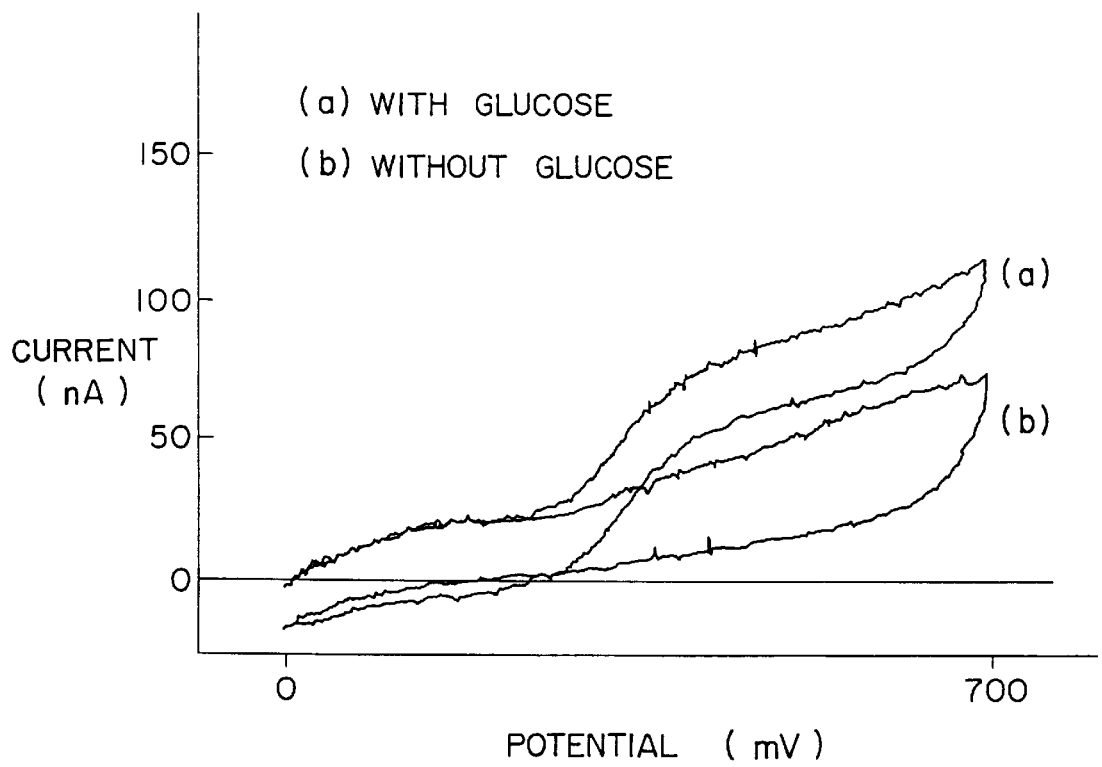
FIG. 8 shows cyclic voltammograms of GOD prepared in Example 6 having ferrocene attached to its body.
Figure 9:
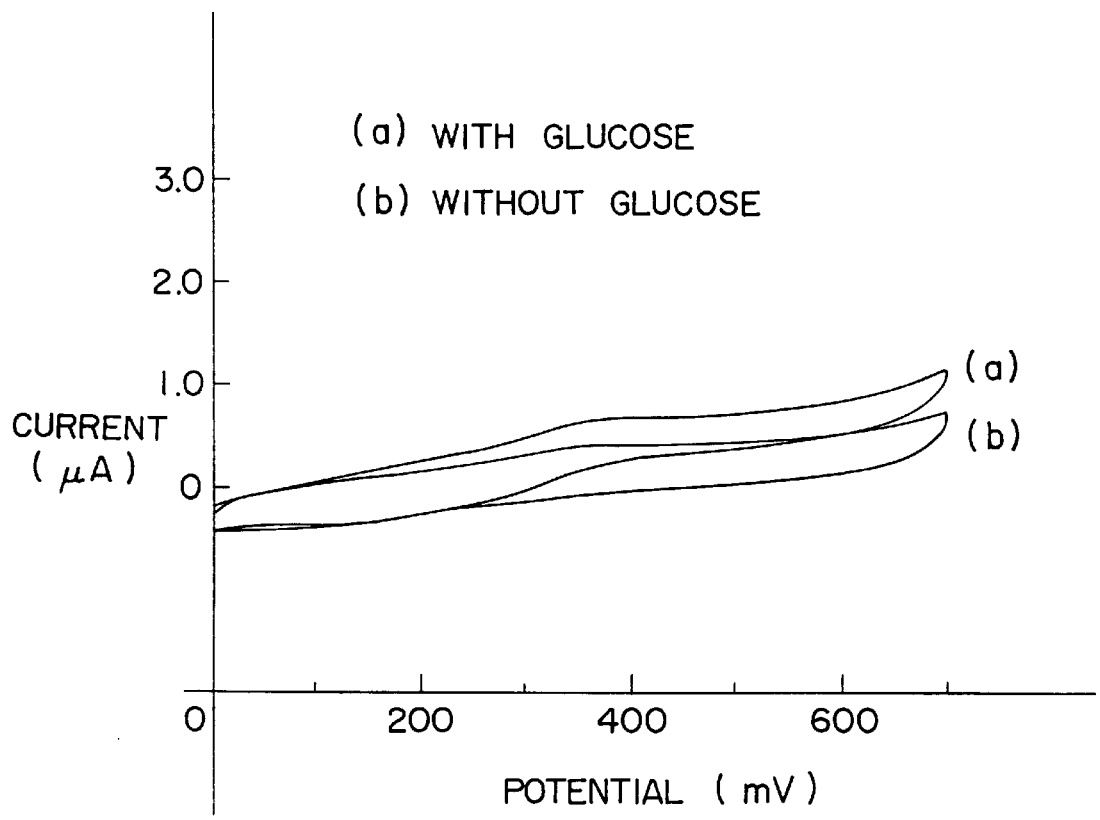
FIG. 9 shows cyclic voltammograms of GOD prepared in Example 7 having ferrocene attached to its body.

The electrically conductive enzymes prepared in Examples 2, 5 and 7 were subjected to measurement of the average number of molecules of ferrocene introduced per molecule of GOD by ICP (Inductively Coupled Plasma Atomic Emission Spectroscopy). As a result, the average number of molecules of ferrocene introduced per molecule of GOD was 11.8, 14.2 and 9.2 respectively for electrically conductive enzymes prepared in Examples 2, 5 and 7. A good correlation was observed between these results and the increase in the electrical conductivity (FIGS. 5, 7 and 9).

COMPARATIVE EXAMPLE 2

A system comprising GOD and a mediator was evaluated in the same manner as that of Example 11. Specifically, the change in the electrical conductivity of the following mixture was measured by using the same valuation apparatus as that used in Example 11.

| | |
|---|---|
| GOD (unmodified) | 100 mg |
| Ferrocene | 1 mg |
| Phosphate buffer (pH 6.0, 0.1 M) | 30 ml |
| Catalase | 3 mg |
| Glucose | 10 mM or 0 mM |

Figure 12:
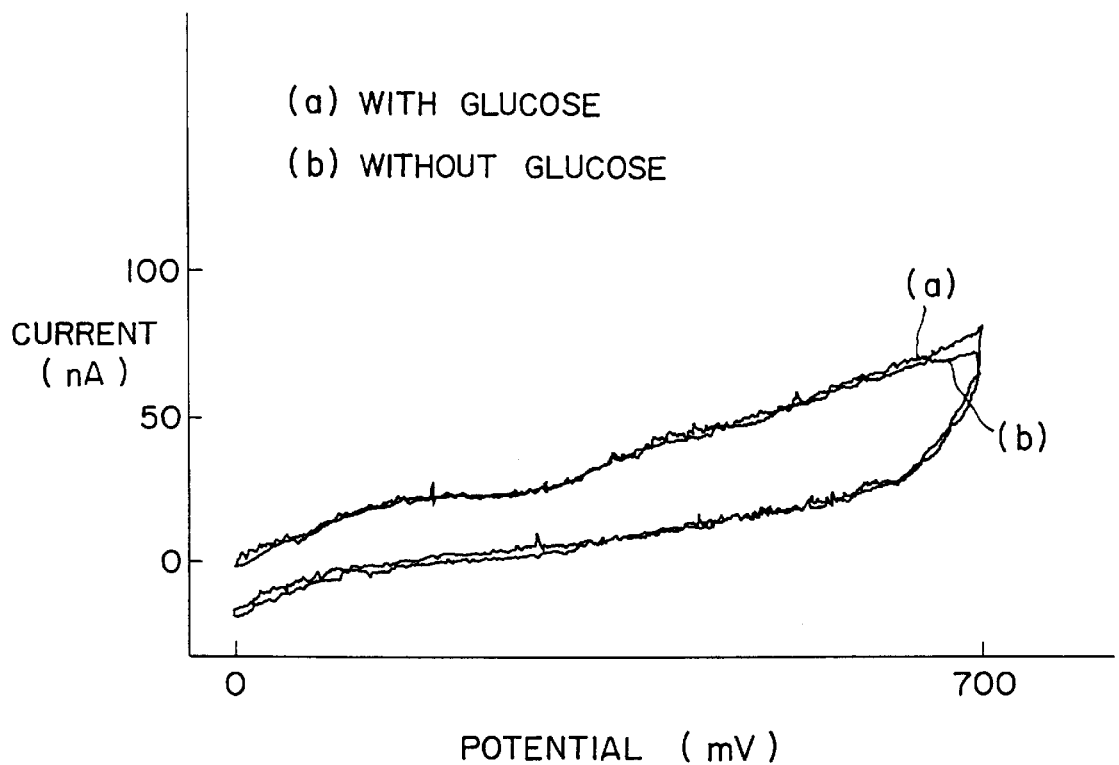
FIG. 12 shows cyclic voltammograms of a system wherein GOD and a mediator are merely present together without bonding.

The results are given in FIG. 12. As is apparent from the drawing, GOD and ferrocene as a mediator hardly contribute to the change in the electrical conductivity of GOD when they are present together in the form of a mere mixture.

EXAMPLE 15

(Preparation of Electrode for Sensor)

An electrically conductive enzyme prepared in Examples 1 to 7 was mixed with the following components to provide composition A. Separately, composition B was prepared in the same manner as that used in the production of composition A, except that use was made of no electrically conductive enzyme.

TABLE 1

| | Composition A | Composition B |
|---|---|---|
| Electrically conductive enzyme | 1.5 g | — |
| Carbon powder | 36.5 g | 36.5 |
| Buffer[1] | 15.0 g | 15.0 g |
| Resin[2] | 20.0 g | 20.0 g |
| Surfactant (Kao Span 20) | 2.0 g | 2.0 g |
| Butyl cellosolve | 15.0 g | 15.0 g |
| Amyl alcohol | 10.0 g | 10.0 g |

Note:
[1] The buffer used was prepared by placing 30 g of citric acid, 120 g of sodium citrate and 504 g of amyl alcohol in a ball mill pot, sufficiently mixing them with each other over a period of 30 hr or more to prepare a slurry.
[2] The resin used was prepared by agitating a mixture of 50.4 g of polyvinylpyrrolidone (Kollidon 90 available from BASF), 9.0 g of polyvinyl butyral (Bx-1 available from Sekisui Chemical Co., Ltd.) and 282.6 g of amyl alcohol by means of an agitator and allowing the mixture to stand overnight.

The compositions A and B were applied to a base material by screen printing to provide two electrodes, that is, a unipolar electrode and a bipolar electrode shown in FIGS. 2(a)–2(d). Specifically, a print of Tetron having a mesh size of 120 mesh and a thickness of 150 μm (available from Mino Group Co., Ltd.) and polystyrene were provided as the screen and the base material, respectively, and screen printing was effected according to a method described in Japanese Patent Laid-Open No. 284661/1986. Immediately after the printing, the print was dried by forced air drying (at room temperature for 5 min), and the base material was then cut into a size of a width of 3 mm, a length of 30 mm and a thickness of 100 mm.

EXAMPLE 16

(Evaluation of Electrodes (1))

Electrodes were evaluated in the same manner as that of Example 11, except that a gold working electrode was used instead of the unipolar electrode prepared in Example 15 and a gold working electrode and a counter electrode were used instead of the bipolar electrode prepared in Example 15. The measurement was effected with the electrode being immersed in the sample by about 20 mm from the side on which no contact was made.

The results of evaluation of the electrodes prepared from compositions containing electrically conductive enzymes prepared respectively in Examples 3 and 9 were as given in the following Tables 2 and 3. Current values in the tables are values of current flowing across the working electrode and the counter electrode when the potential difference was +450 mV.

TABLE 2

| Glucose concentration (mM) | 0 | 5 | 5 |
|---|---|---|---|
| Unipolar electrode | 79 nA | 130 nA | 176 nA |
| Bipolar electrode | 75 nA | 102 nA | 127 nA |

TABLE 3

| Fructose concentration (mM) | 0 | 5 | 5 |
|---|---|---|---|
| Unipolar electrode | 60 nA | 64 nA | 66 nA |
| Bipolar electrode | 45 nA | 52 nA | 55 nA |

EXAMPLE 17

(Evaluation of Electrodes (2))

Electrically conductive enzymes prepared in Examples 2, 5 and 7 were mixed with components specified in Table 4 to provide composition C. Further, composition D was provided in the same manner as that used in the production of composition C, except that use was made of unmodified GOD and ferrocenecarboxylic acid.

TABLE 4

| | Composition C | Composition D | |
|---|---|---|---|
| Conductive enzyme | 0.610 | GOD | 0.603 |
| | | Ferrocene | 0.007 |
| Buffer | 10.000 | 10.000 | |
| Surfactant | 1.180 | 1.180 | |
| Resin | 14.040 | 14.040 | |
| Crystalline cellulose | 28.140 | 28.140 | |
| Carbon powder | 30.000 | 30.000 | |
| Amyl alcohol | 16.030 | 16.030 | |
| | 100.000 | 100.000 | |

Figure 14:
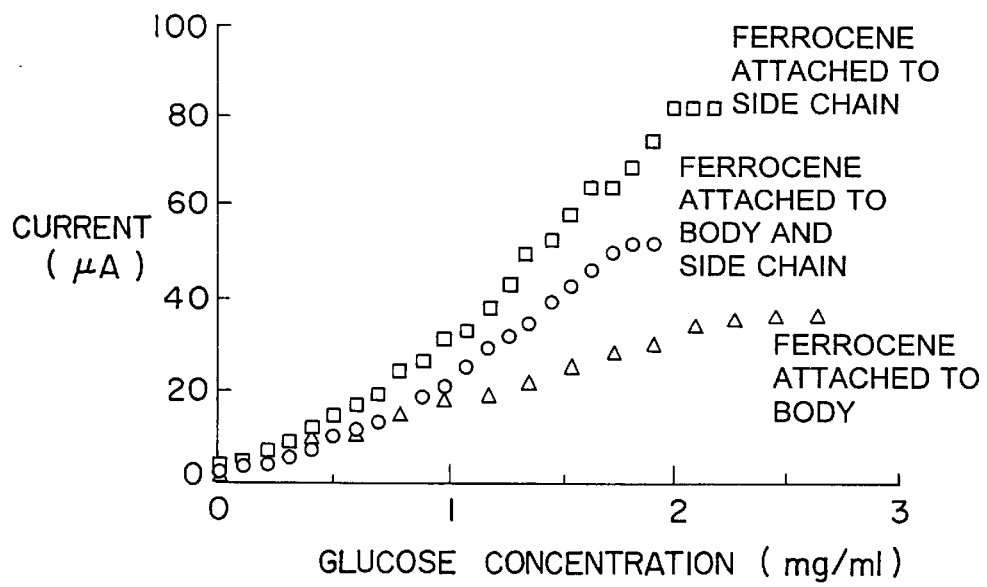
FIG. 14 is a graph showing the relationship between the current value and the concentration of glucose with an electrode on which GOD having ferrocene attached to its side chain has been immobilized (□), an electrode on which GOD having ferrocene attached to its body and side chain has been immobilized (○) and an electrode on which GOD having ferrocene attached to its body has been immobilized (Δ)

Composition C was subjected to screen printing in the same manner as that of Example 15, except that a 5 mm square pattern was used as the screen and a polyamide film was used as the base material, thereby forming 12 electrodes in total on the base material as shown in FIG. 13(*a*). One electrode as shown in FIG. 13(*b*) was cut off from the base material, and this electrode was subjected to evaluation of the relationship between the glucose concentration and the current value in the same manner as that of Example 16, except that the potential difference was +700 mV. The results were as shown in FIG. 14.

COMPARATIVE EXAMPLE 3

Figure 15:
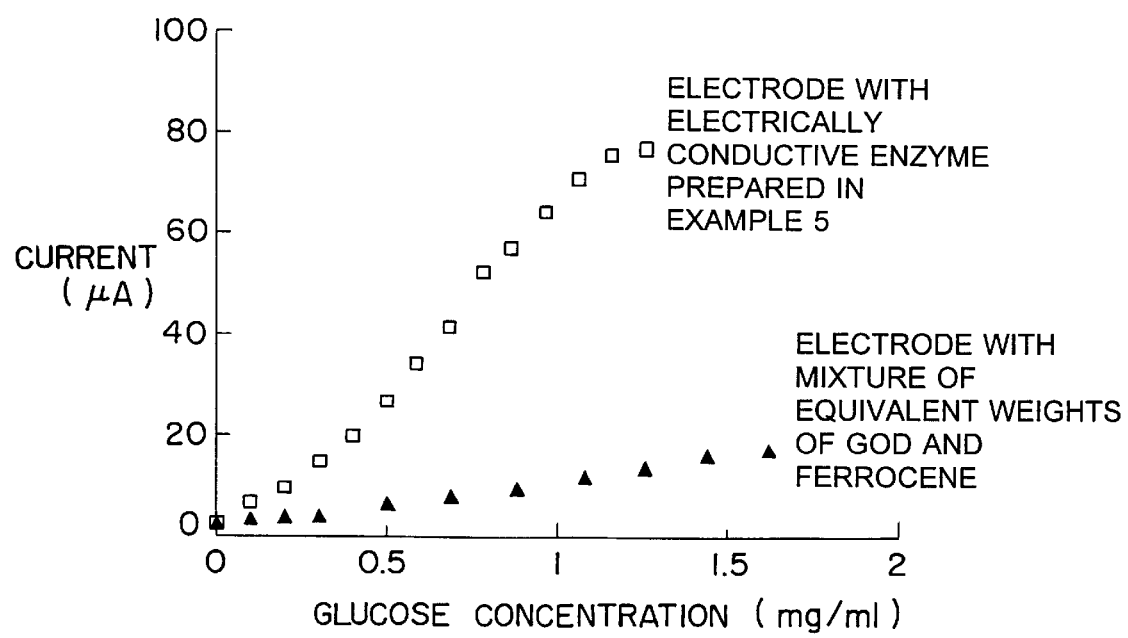
FIG. 15 is a graph showing the relationship between the current value and the concentration of glucose with an electrode on which an electrically conductive enzyme prepared in Example 5 has been immobilized (□) and an electrode on which a mixture of equivalent weights of GOD and ferrocene has been immobilized (▲).

An electrode was prepared in the same manner as that of Example 17, except that composition D was used instead of composition C and a 7 mm square pattern was used as the screen. The relationship between the glucose concentration and the current value for the electrode produced from the composition D was compared with that for the electrode produced from the composition C containing the electrically conductive enzyme prepared in Example 5. The results were shown in FIG. 15.

What is claimed is:

1. A process for producing an electrically conductive enzyme comprising an enzyme and a mediator attached to a side chain and the body of the enzyme through a covalent bond wherein said enzyme is glucose oxidase and said mediator is a ferrocene derivative attached to the side chain of the enzyme through a spacer, comprising the steps of oxidizing a glucose oxidase with an oxidizing agent to form an aldehyde group on an oligosaccharide of the glucose oxidase;

reacting said glucose oxidase with a dihydrazide represented by the following formula (II):

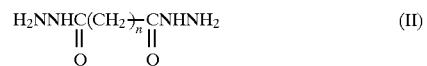

wherein n is an integer of 1 to 7; and reacting the reaction product with a ferrocenecarboxylic acid.

2. An enzyme-immobilized electrode comprising a base material and an electrically conductive enzyme obtained by the process according to claim 1, the enzyme being immobilized on the base material.

3. A composition for preparing an enzyme-immobilized electrode, comprising an electrically conductive enzyme obtained by the process according to claim 1, an electrically conductive component and a vehicle.

4. A process for preparing an enzyme-immobilized electrode which comprises immobilizing the composition according to claim 3 on a base material.

5. A process according to claim 4, wherein the composition is immobilized on the base material by a printing technique selected from the group consisting of a screen printing and roller coating and with dispenser.

6. The process for producing an electrically conductive enzyme according to claim 1, wherein said reacting is carried out in the presence of a reducing agent or a condensing agent.

7. A process for preparing an enzyme-immobilized electrode which comprises immobilizing a composition on a base material, the composition comprising an electrically conductive enzyme, an electrically conductive component and a vehicle.

* * * * *